United States Patent [19]

Hogan

[11] Patent Number: 4,943,283
[45] Date of Patent: Jul. 24, 1990

[54] BLOOD COLLECTING APPARATUS WITH SHIELDED NEEDLES

[75] Inventor: J. Martin Hogan, Long Beach, Calif.

[73] Assignee: City of Hope, Duarte, Calif.

[21] Appl. No.: 221,603

[22] Filed: Jul. 20, 1988

[51] Int. Cl.$^5$ ............................................. A61M 5/32
[52] U.S. Cl. .................................... 604/198; 604/263; 604/412; 604/905
[58] Field of Search ............................ 604/408–414, 604/905, 198, 263; 128/763–768

[56] References Cited

U.S. PATENT DOCUMENTS

| | | | |
|---|---|---|---|
| 3,127,892 | 4/1964 | Bellamy et al. | 604/412 X |
| 3,217,710 | 11/1965 | Beall et al. | 604/412 X |
| 3,654,924 | 4/1972 | Wilson et al. | 604/409 X |
| 4,511,359 | 4/1985 | Vaillancourt | 604/411 |
| 4,655,741 | 4/1987 | Kamishima | 604/412 X |
| 4,676,783 | 6/1987 | Jagger et al. | 604/171 |
| 4,820,282 | 4/1989 | Hogan | 604/263 |

OTHER PUBLICATIONS

"Blood-Pack Unit Configurations", Fenwal Laboratories, Deerfield, Ill.
"Blood-Pack Units with SID (Separate Integral Donor) Tubing", Fenwal Laboratories, Deerfield, Ill.
"Fenwal Introdcues Blood-Pack Units with PL 1240 Plastic Satellite Containers for 5 Day Platelet Storage",
Fenwal Laboratories Physical Specimen of Blood Bag Produced by Cutter, a division of Miles Laboratories.

Primary Examiner—C. Fred Rosenbaum
Assistant Examiner—C. Maglione
Attorney, Agent, or Firm—Edward S. Irons

[57] ABSTRACT

An apparatus for collecting blood or other body fluid from a donor, in which a length of tubing has a first needle on one end for insertion into the vein of a donor, and a frangible joint between the ends of the tubing to separate the length of tubing into first and second parts. The frangible joint includes a combination needle shield and test tube receptacle on one end of the first part, disposed coaxially to a second needle used to fill test tubes with material drawn through the first needle. The combination shield and test tube receptacle is adapted to receive a test tube therein for operative relationship with the second needle so that the test tube may be filled with the material. A second shield is slidable on the tubing and has a retracted position adjacent the frangible joint and an operative position extended over the first needle when that needle is withdrawn from the vein. Another form of the invention involves a length of tubing provided with only a donor needle and a combination test tube receptacle and needle shield.

8 Claims, 5 Drawing Sheets

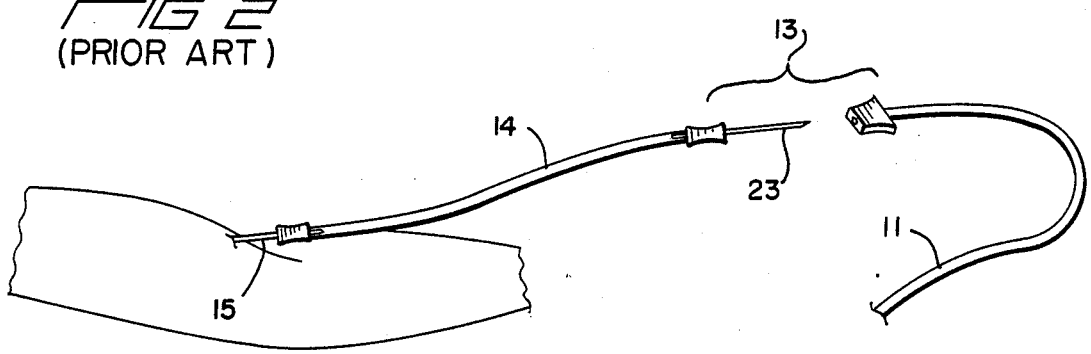
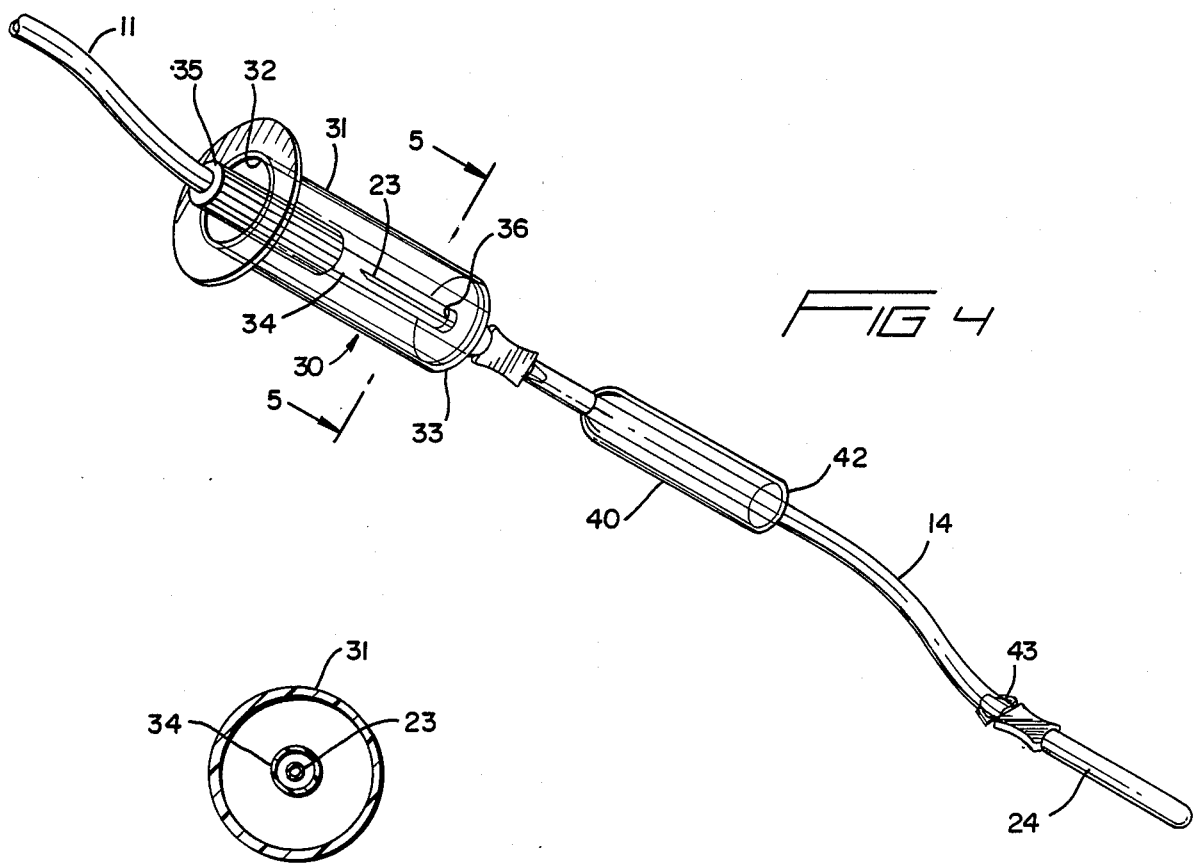

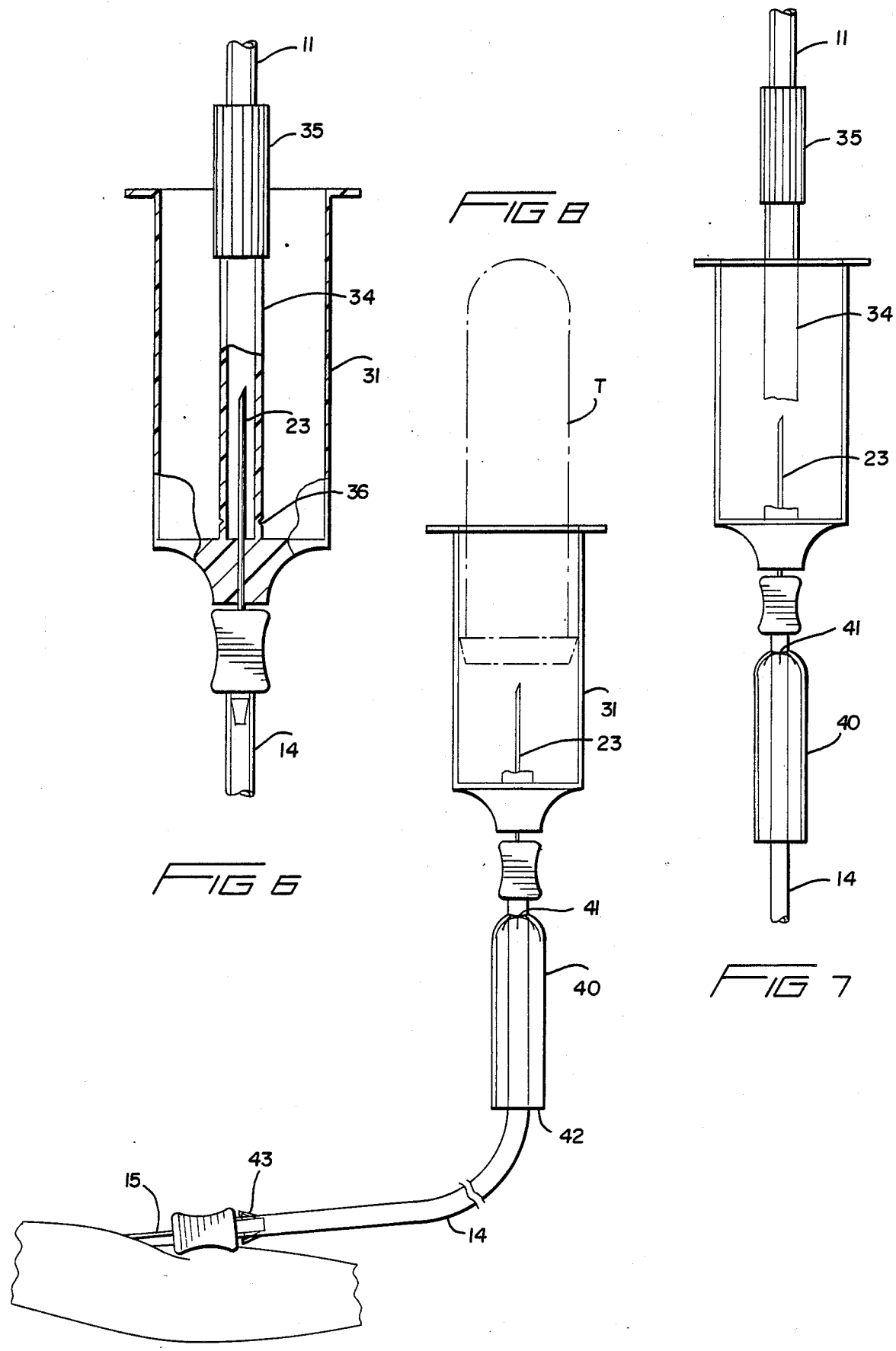

BLOOD COLLECTING APPARATUS WITH SHIELDED NEEDLES

FIELD OF THE INVENTION

This invention relates to apparatus for collecting blood or other body fluids, and more particularly, to a biological blood bag system for collecting blood from the vein of a donor.

BACKGROUND OF THE INVENTION

In the collection and testing of blood, various apparatus and methods are used. One such system uses a primary blood bag connected through a first length of tubing to a needle which is inserted into the vein of a donor to draw blood from the vein and into the bag. A second length of tubing is connected at one end with the blood bag and at its other end to a Y-connector, which, in turn, is connected through further lengths of tubing to a pair of red cell storage bags.

When the blood bag has been filled, the first length of tubing is clamped adjacent the blood bag and separated between the clamp and the needle, which remains in the donor's vein. When the tubing is separated, a second needle is exposed, connected to that portion of the tubing which remains connected to the needle in the donor's vein. This second needle is then used to fill test tubes for various blood screening tests. The exposed second needle constitutes a risk to health workers.

After the test tubes are filled, the first needle is removed from the vein of the donor, thus exposing that needle and creating a further risk to health workers.

SUMMARY OF THE INVENTION

It is therefore an object of this invention to provide a blood collecting system in which the needles used for piercing the vein of a donor and for filling test tubes with blood for various screening tests are shielded during use.

Another object of the invention is to provide a system for collecting blood or other body fluids, in which a length of tubing extends between a blood bag and a needle used for piercing the vein of a donor to fill the bag, and said tubing is then separable to expose a second needle connected with the first needle and used to fill test tubes for various screening tests on the blood, wherein shields are provided in association with said first and second needles to protect health workers against accidental contact with the needles.

A further object of the invention is to provide a shielded needle system for collecting blood, in which a length of tubing has a needle at one end for insertion into the vein of a donor, and a separable portion between the ends including a second needle which can be exposed to fill test tubes with blood drawn through the first needle, and wherein said separable portion includes a shield which remains in protective relationship around the second needle after separation of the tubing and a movable shield is slidable along the tubing to surround and shield the first needle while and after it is withdrawn from the vein of the donor.

An even further object of the invention is to provide a shield for the needle in a blood collecting system which is used to fill test tubes with blood for various screening tests. The shield comprises a tubular body surrounding the needle and is adapted to receive the test tube therein for operative association with the shielded needle.

Another object of the invention is to provide a shield for a needle used to collect blood or other body fluid, wherein the shield is movable along a length of tubing connected with the needle to surround the needle as the needle is being withdrawn from the vein of a donor.

These objects are achieved by a unique blood collection system in which a blood bag is connected through a length of tubing with a first needle to be inserted into the vein of a donor to draw blood from the vein. The length of tubing includes a separable portion between its ends which is disassembled after the bag is filled, for exposing a second needle used to fill test tubes with blood from the first needle. A rigid tubular shield comprises part of the separable portion and remains in surrounding relationship to the second needle after the tubing is separated. The shield is adapted to receive the test tube for operative association with the shielded needle.

A second shield of tubular configuration is slidable along the length of tubing into surrounding relationship with the first needle as the needle is being withdrawn from the vein of the donor, and is engageable behind detent means to retain the shield in protective relationship with the first needle.

BRIEF DESCRIPTION OF THE DRAWINGS

The foregoing and other objects and advantages of the invention will become apparent from the following detailed description and accompanying drawings, in which like reference characters designate like parts throughout the several views, and wherein:

FIG. 2 is a somewhat schematic view of a portion of the system of FIG. 1, showing the first needle inserted into the vein of the donor, and the length of tubing being separated to expose the second needle.

FIG. 3 is a view of the separated length of tubing in FIG. 1 with both the first and second needles exposed.

FIG. 4 is a fragmentary perspective view of a portion of the first length of tubing in a system such as shown in FIG. 1, but with the needle shields of the invention.

FIG. 5 is an enlarged transverse sectional view taken along line 5—5 in FIG. 4.

FIG. 6 is an enlarged fragmentary view, shown partly in section, of a frangible separable portion of the system of the invention.

FIG. 7 is an enlarged fragmentary view in elevation of the frangible section of the invention being separated to expose the second needle for use.

FIG. 8 is an enlarged fragmentary view in elevation showing how a test tube is inserted into the second needle shield for operative association with the second needle.

DETAILED DESCRIPTION OF THE PREFERRED EMBODIMENT

Figure 1:
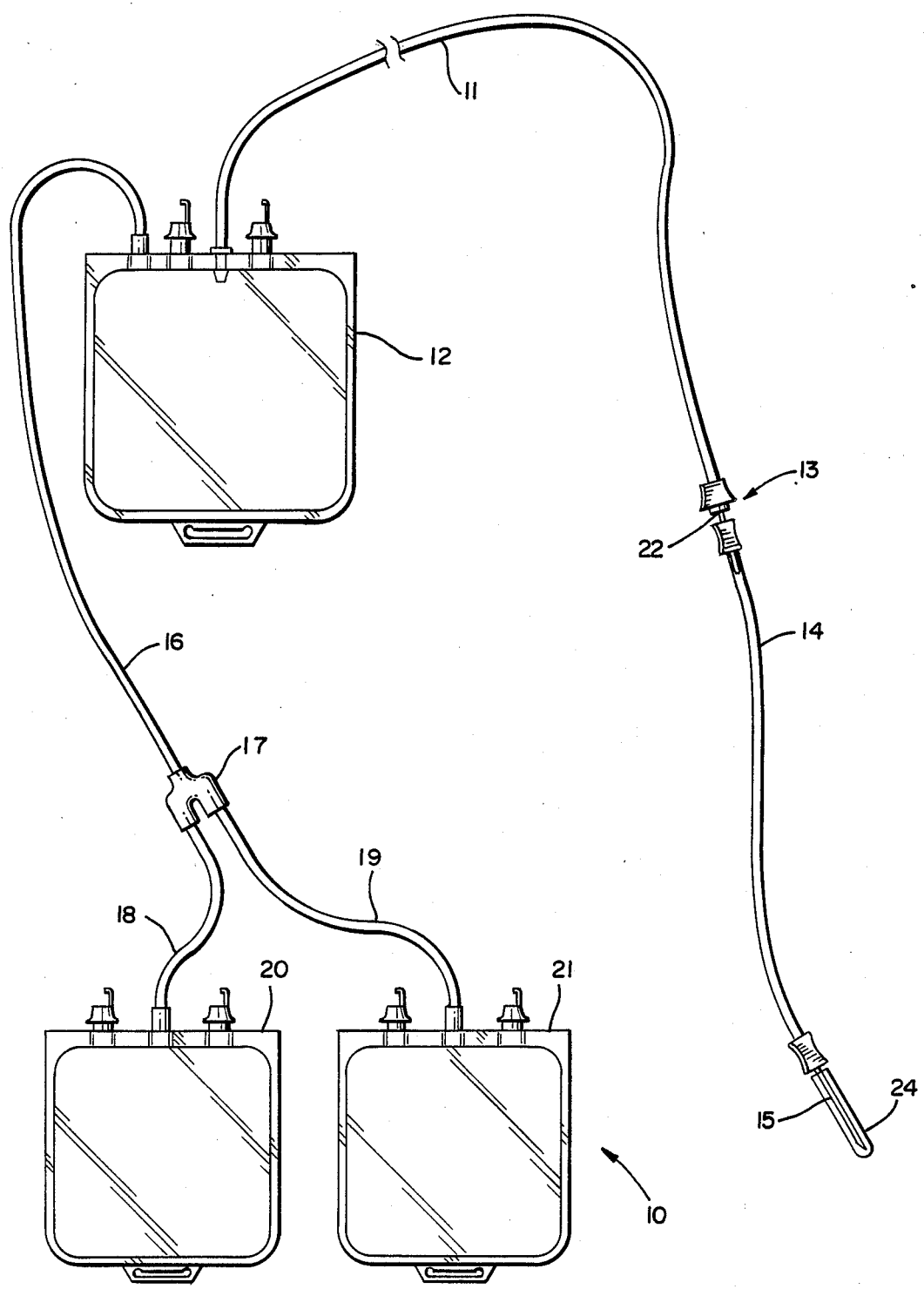
FIG. 1 is plan view of an assembled prior art system.
Figure 9:
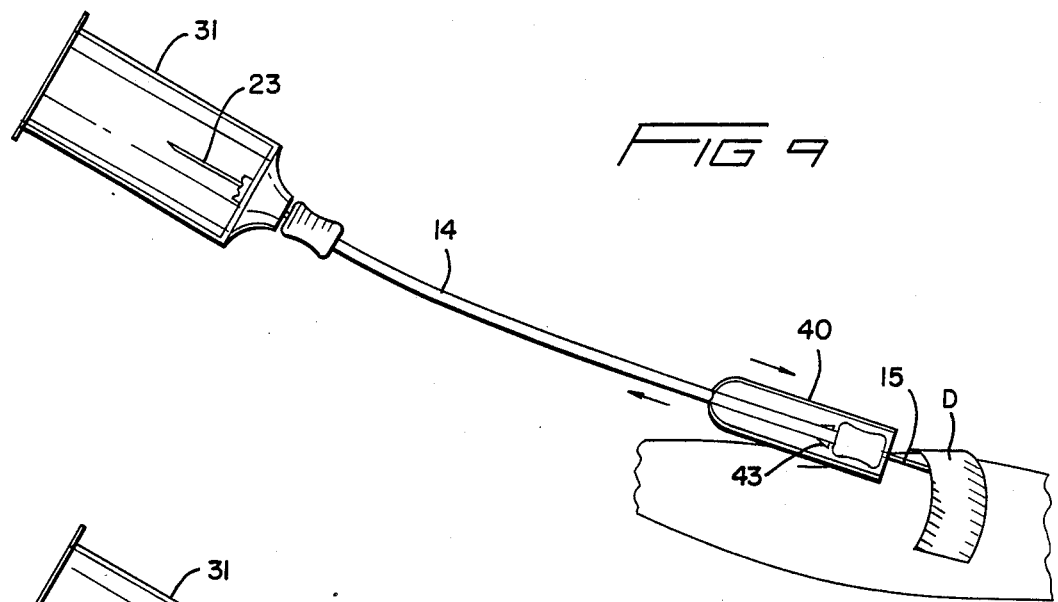
FIG. 9 is a view in elevation showing the shield for the first needle being moved into position to receive the first needle as it is withdrawn from the vein of the donor.
Figure 10:
FIG. 10 is a view of the separated length of tubing of the blood collection system of the invention, with both needle shields in place over their respective needles.
Figure 11:
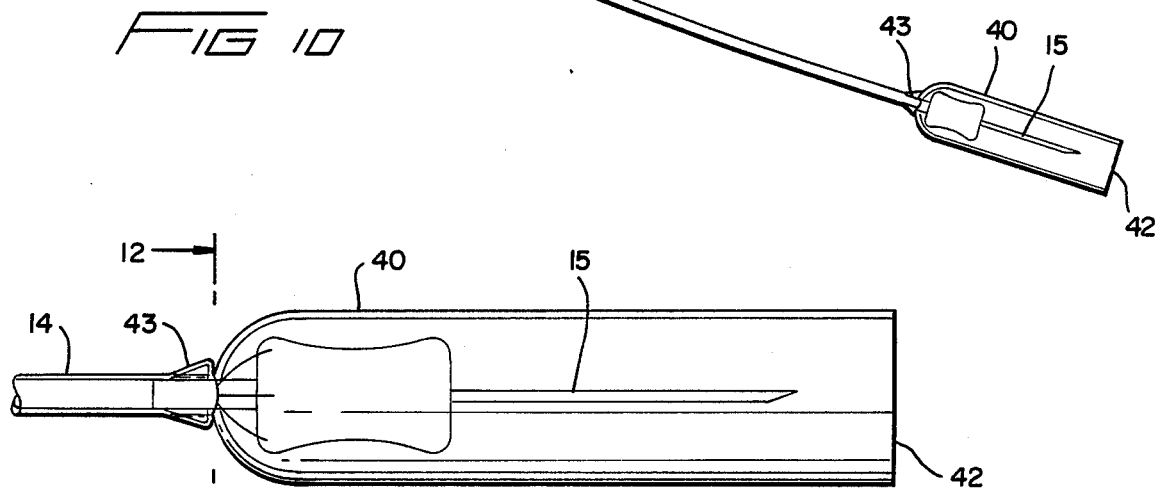
FIG. 11 is a greatly enlarged view in side elevation depicting the shield over the first needle, and showing how the shield is engaged behind the shield detent.

Referring more specifically to the drawings, a prior art blood bag system for collecting blood from the vein of a donor is indicated generally at 10 in FIGS. 1-3. In this system, a first distal tube 11 is connected with a blood bag 12 and through a sealed needle joint 13 with a second distal tube 14 and needle 15 for insertion into the vein of a patient. A second length of tubing 16 extends from the blood bag to a Y-connector 17 and thence through two further lengths of tubing 18 and 19 with red cell storage bags 20 and 21.

The sealed needle joint 13 includes a frangible portion 22 connecting the two sections of tubing, and a needle 23 which is confined within the joint prior to separation of the tubing sections. A cap 24 is placed over the needle 15 to shield that needle prior to use.

In practice, the cap 24 is removed from needle 15 and that needle is then inserted into the vein of a donor to draw blood from the donor. After the blood bag 12 is filled, the distal tube 11 is clamped and separated from the distal tube 14 by breaking the frangible seal 22, exposing the needle 23. Needle 23 is then used to fill vacutainer test tubes for various blood screening tests. Distal tube 14 may be clamped or unclamped to permit or restrict the flow of blood. During this time, needle 15 remains in the vein of the donor, but needle 23 is exposed, creating a hazard to health workers. After the test tubes are filled, needle 15 is removed from the vein of the donor for disposal of the length of tubing and needles carried on the ends, thereby exposing the needle 15 and creating a further hazard to the health workers.

In the system of the invention, as shown in FIGS. 4—10, the sealed needle joint 13 of the prior art is replaced with a separable connection 30 including a Vacutainer type barrel 31 having an open end 32 and a closed end 33. Although the separable connection is shown as frangible, it may take a different form such as a threaded or bayonet connection. Needle 23 connected with distal tube 14 extends through the closed end of the barrel where it is fixed and is confined within and shielded by the barrel. It should be noted that the Vacutainer brand barrel 31 is a modified version of one component of a two part system by Becton-Dickinson Corp., in which the barrel normally has a needle fixed in the closed end, and a glass test tube with a rubber seal in the open end is adapted to be inserted in close-fitting relationship in the barrel so that the rubber seal can be pierced by the needle carried in the barrel. The barrel 31 in the present invention eliminates the needle as conventionally used on the prior art apparatus, and instead incorporates the needle 23 carried on the distal tube 14.

A rigid, frangible tube 34 is permanently affixed at one end to the closed end of the barrel and extends coaxially through the barrel to a knurled grip 35 which connects the end of the frangible tube with the distal tube 11 and which projects beyond the end of the barrel so that it may be grasped to break the frangible connection. A threaded or bayonet connection may alternatively be utilized. Thus, blood drawn from a vein of the donor through needle 15 is enabled to flow through the distal tube 14, frangible connection 30 and distal tube 11 to the blood bag 12.

When the blood bag is filled, the distal tube 11 is clamped and the knurled grip twisted to twist the tube 34 and break it at weakened area 36, thereby exposing the needle 23 within the barrel. Vacutainer brand test tube "T" are then inserted into the barrel into operative relationship with the needle 23 so that they can be filled with blood for various screening tests. The needle 23 thus remains shielded at all times from contact with health workers, eliminating the danger which is presented by exposure of this needle in prior art devices. During this time, the needle 15 remains inserted in the vein of the donor. The tube 14 may be clamped to stop the flow of blood while changing test tubes.

Figure 12:
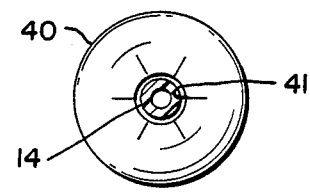
FIG. 12 is an enlarged transverse sectional view taken along line 12—12 in FIG. 11.

After the test tubes are filled, a pressure dressing "D" may be placed over the venipuncture site and needle 15 withdrawn from the vein of the donor. Prior to removal of the needle, however, a tubular shield 40 is moved from its retracted position adjacent the frangible connection 30 to a position immediately adjacent the venipuncture site. The tubular shield 40 has a relatively narrow opening 41 in one end, closely surrounding the distal tube 14, and a wider end 42 which is adapted to slide over the needle 15 and associated components. The length of the shield is such that it will project beyond the sharpened end of the needle 15 when it is slid fully down over the needle. A detent 43 is formed at the juncture of needle 15 with distal tube 11, to lock the shield 40 in place over the needle 15 after it has been slid down over the needle. Further, as seen in FIG. 12, the shield 40 may be radially slit around the opening 41 to facilitate movement of the shield over the detent 43. Thus, health workers are protected at all times against exposure to the sharpened point of needle 15. A plug or cap, not shown, may additionally be fixed to the opening 32 to further protect against injury. Said cap or plug may be hinged or otherwise attached to the barrel 31.

A butterfly or winged needle could be used in lieu of the needle 15, if desired, and rather than the slidable tubular shield 40, a shield envelope such as described in copending application Ser. Nos. 101,428 (continuation-in-part of Ser. No. 920,613) and 133,241 (continuation of Ser. No. 920,613) may be used.

Figure 13:
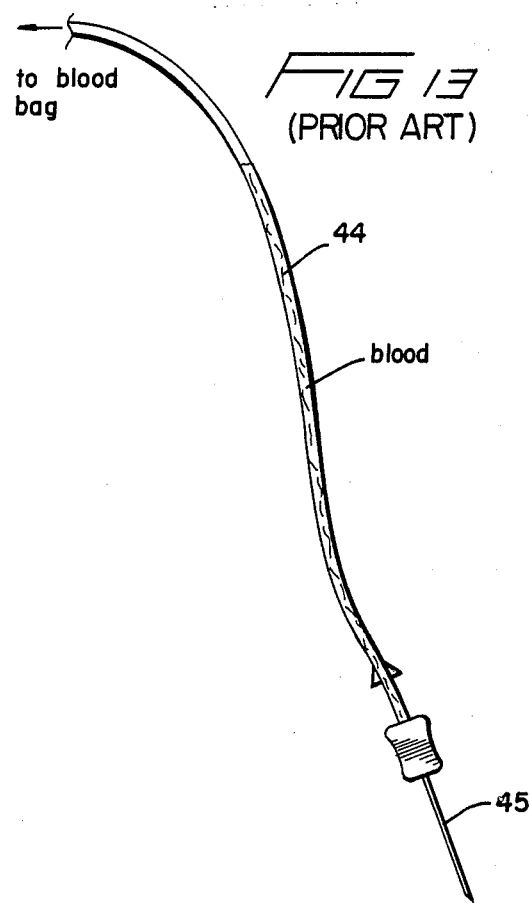
FIG. 13 is a partial plan view of another form of prior art device.

A different form of prior art blood collecting system is shown by FIG. 13 which employs only a distal (donor) needle.

Referring to FIG. 13, the bag is first filled with blood. Thereafter, non-heparinzed blood is expressed back through the tube 44 only through the needle 45 to fill sample test tubes.

Figure 14:
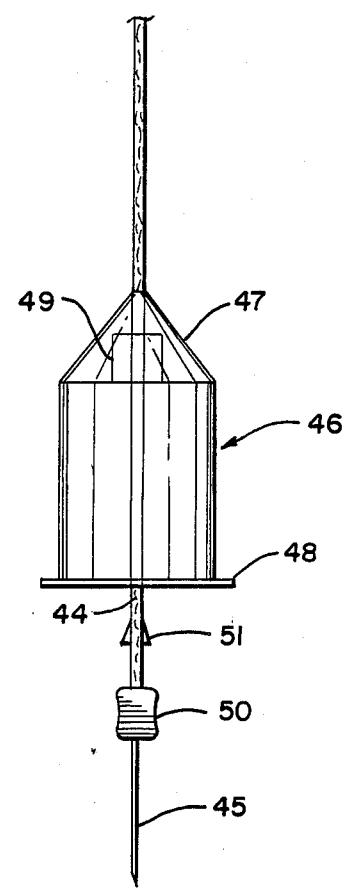
FIG. 14 is a plan view of a form of the invention useful in connection with a prior art device as shown in FIG. 13.
Figure 15:
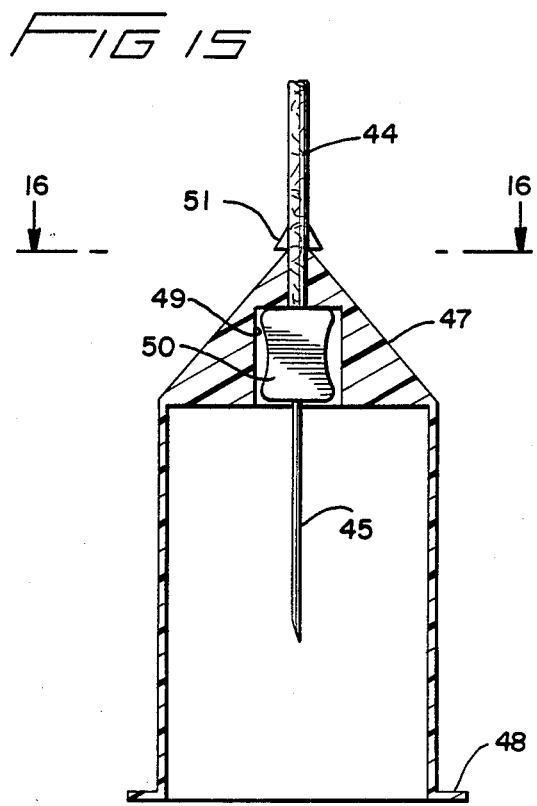
FIG. 15 is a view of the apparatus shown in FIG. 14 with the vacutainer shield in position over a donor needle.
Figure 16:
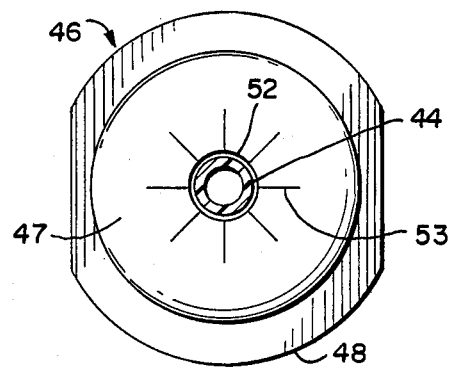
FIG. 16 is an enlarged transverse section taken along the line 16—16 of FIG. 15.

FIGS. 14, 15 and 16 illustrate an embodiment of the invention useful with a single needle blood collecting system of the kind illustrated by FIG. 13.

Referring to FIG. 14, a modified vacutainer barrel 46 is provided with means 47 for engaging tube 44 at its upper end and with an open lower end 48 for the receipt of vacutainer test tubes. The means 47 for engaging the tube 44 is recessed at 49 to receive the top side of the needle shank 50. The tube 44 is provided with detents 51 spaced above the needle shank.

FIG. 14 shows the tube 44 filled with blood. The vacutainer barrel 46 is positioned on blood-filled tube 44 a substantial distance above the needle shank 50.

FIG. 15 shows the vacutainer barrel 46 moved downwardly over the needle 15 and locked into position by the abutment of the top of the needle shank 50 with the recess 49 in the upper tube engaging means 47. As shown in FIG. 16, open end 52 with radial slits 53 provide a tube engaging means to allow the lock to engage detents 51.

With the vacutainer shield locked into the position shown in FIG. 15, blood may be drained retrograde from the tube 44 to fill sample test tubes without risk to health workers. The modified vacutainer barrel 46 functions as a combination needle shield and test tube receptacle. A plug or cap, not shown, may additionally be fixed to the opening 48 to further protect against injury. Said cap or plug may be hinged or otherwise attached to the barrel 46.

Although the invention has been described with reference to particular embodiments, it is to be understood that this embodiment is merely illustrative of the application of the principles of the invention. Numerous modifications may be made therein and other arrangements may be devised without departing from the spirit and scope of the invention.

I claim:

1. In an apparatus for collecting blood or other body fluids, wherein a length of tubing has a needle on one end for insertion into the vein of a donor and for filling test tubes with blood for various screening tests, the improvement comprising:

a combination needle shield and test tube receptacle mounted for movement along a length of said tubing from a position spaced from said needle while inserted into the vein of a donor to a shielding position to protect health workers against exposure to the sharpened point of the needle and to receive a test tube for operative association with the needle so that the test tube may be filled with blood or other body fluid.

2. In an apparatus for collecting blood or other body fluids, wherein a first length of tubing has a first needle on one end for insertion into the vein of a donor and a second needle on the other end for filling test tubes with blood for various screening tests, the improvement comprising:

a combination needle shield and test tube receptacle on the length of tubing in shielding relationship to the second needle to protect health workers against exposure to the sharpened point of the needle and to receive a test tube for operative association with the needle so that the test tube may be filled with blood or other body fluid, said combination needle shield and test5 bue receptacle comprising part of a frangible needle seal for joining said first length of tubing with a second length of tubing, said frangible needle seal including a rigid frangible tube fixed at one end to one end of the shield and extending coaxially therewithin and over said needle, said frangible tube being fixed at its other end to the second length of tubing and being joined to said shield through a weakened area so that the tube may be broken from the shield and removed, to separate the second length of tubing from the first length of tubing and to expose the needle inside the shield.

3. An apparatus as claimed in claim 2, wherein:
a knurled grip is on said other end of said rigid frangible tube to facilitate grasping thereof to break the weakened area.

4. An apparatus as claimed in claim 3, wherein:
a tubular sheath is slidably positioned on the first length of tubing and has a retracted position adjacent the combination needle shield and test tube receptacle, and an operative position disposed in shielding relationship over the first needle.

5. An apparatus as claimed in claim 5, wherein:
detent means is formed near the juncture of said first needle and the first length of tubing for cooperation with the tubular shield to retain the shield in position over the first needle.

6. An apparatus as claimed in claim 5, wherein:
said combination needle shield and test tube receptacle comprises one component of a two part system for filling evacuated test tubes.

7. An apparatus as claimed in claim 6, wherein
the second length of tubing is connected with a blood bag for collecting blood drawn from the vein of a donor through the first needle; and
said blood bag is connected with two red cell storage bags through further tubing and a Y-connector.

8. AN apparatus for collecting a body fluid and for providing sequential test tube samples of said fluid comprising:
a length of tubing,
a first needle at one end of the tubing for insertion into a patient's body for removal of said body fluid,
a second needle at the other end of said tube through which said body fluid may flow, and
a rigid, tubular shield mounted on said length of tubing in surrounding relationship to said second needle, said shield being sized to accommodate the insertion of a test tube into operative association with said second needle for receipt of said body fluid flowing from a patient into and through said first needle, said tubing and said second needle.

* * * * *